(12) United States Patent
Heeres

(10) Patent No.: US 7,741,358 B2
(45) Date of Patent: Jun. 22, 2010

(54) CRYSTAL FORM OF ASENAPINE MALEATE

(75) Inventor: Gerhardus Johannes Heeres, Oss (NL)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 11/399,204

(22) Filed: Apr. 6, 2006

(65) Prior Publication Data

US 2007/0027134 A1  Feb. 1, 2007

Related U.S. Application Data

(60) Provisional application No. 60/671,782, filed on Apr. 14, 2005.

(51) Int. Cl.
*A61K 31/40* (2006.01)
*A01N 43/38* (2006.01)
*C09B 5/00* (2006.01)

(52) U.S. Cl. .................................. 514/410; 548/416

(58) Field of Classification Search ................ None
See application file for complete search history.

(56) References Cited

U.S. PATENT DOCUMENTS

| | | | |
|---|---|---|---|
| 4,145,434 A | 3/1979 | van der Burg | 424/274 |
| 4,154,386 A * | 5/1979 | Kawada | 226/91 |
| 4,481,205 A | 11/1984 | Von Bebenburg et al. | |
| 4,786,735 A | 11/1988 | Grayboes et al. | |
| 5,534,522 A | 7/1996 | Ando et al. | |
| 5,763,476 A | 6/1998 | Delbressine et al. | 514/410 |
| 2006/0084692 A1 | 4/2006 | Wong et al. | |
| 2006/0229352 A1 | 10/2006 | Kemperman | |

FOREIGN PATENT DOCUMENTS

| | | |
|---|---|---|
| WO | WO 95/23600 A1 | 9/1995 |
| WO | WO 99/32108 A1 | 7/1999 |
| WO | WO 2004/110437 A1 | 12/2004 |

OTHER PUBLICATIONS

Mortimer, Ann. Expert Opinion on Investigational Drugs, 2004, 13(4), 315-329.*
Vervoort el al. Journal of Chromatography A, 1994, 678(1) 1-15.*
Broekkamp et al. Drug Research, 1990, 40(5), 544-49.*
DeBoer et al. Drug Research, 1990, 40(5), 550-554.*
Room et al. European Journal of Pharmacology, 1991, 205, 233-40.*
European Search Report for Application No. EP 06 11 2332 dated Aug. 14, 2006.
Vader, J. et al., "The Syntheses of Radiolabelled Org 5222 and Its Main Metabolite Org 30526," Journal of Labelled Compounds and Radiopharmaceuticals, vol. 34, No. 9 (1994) pp. 845-869.
De Boer, Th. et al., Org-5222 "Antipsychotic Dopamine $D_2$ Receptor Antagonist 5-$HT_2$ Receptor Antagonist," Drugs of the Future, vol. 18, No. 12 (1993) pp. 1117-1123.
Funke, C. W. et al., "Physico-chemical Properties and Stability of trans-5-Chloro-2-methyl-2,3,3a,12b-tetrahydro-1H-dibenz[2,3:6,7]oxepino[4,5-c]pyrrolidine Maleate," Arzneim.-Forsch./Drug Res., vol. 40, No. 5 (1990) pp. 536-539.

* cited by examiner

*Primary Examiner*—James O Wilson
*Assistant Examiner*—Noble Jarrell
(74) *Attorney, Agent, or Firm*—H. Eric Fischer; Gerard Devlin

(57) ABSTRACT

The invention relates to an orthorhombic crystal form of compound trans-5-chloro-2,3,3a,12b-tetrahydro-2-methyl-1H-dibenz [2,3:6,7]oxepino[4,5-c]pyrrole (Z)-2-butenedioate, to methods for the preparation of this crystal form and to pharmaceutical compositions comprising an orthorhombic crystal form.

11 Claims, 2 Drawing Sheets

CRYSTAL FORM OF ASENAPINE MALEATE

This application claims priority based on U.S. Provisional Patent Application No. 60/671,782, filed Apr. 14, 2005.

The invention relates to a new crystal form of asenapine, to methods for the preparation thereof and to pharmaceutical compositions comprising said crystal form.

Asenapine is a compound for use in the treatment of central nervous system disorders, in particular schizophrenia. The chemical name of asenapine is trans-5-chloro-2-methyl-2,3,3a,12b-tetrahydro-1H-dibenz[2,3:6,7]oxepino[4,5-c]pyrrole and the preparation thereof is disclosed in U.S. Pat. No. 4,145,434.

Asenapine is being developed as its maleate salt 2. This salt is prepared by adding one molar equivalent of an ethanolic solution of maleic acid to an ethanolic solution of asenapine 1, according to example 1. For further purification, the thus obtained asenapine maleate 2, can be recrystallized from ethanol.

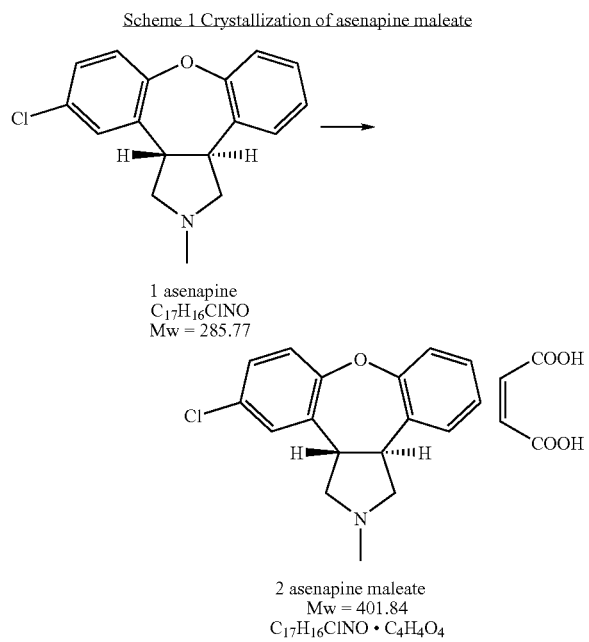

Scheme 1 Crystallization of asenapine maleate 1 asenapine
$C_{17}H_{16}ClNO$
Mw = 285.77

2 asenapine maleate
Mw = 401.84
$C_{17}H_{16}ClNO \cdot C_4H_4O_4$

The pharmacological profile of trans-5-chloro-2-methyl-2,3,3a,12b-tetrahydro-1H-dibenz[2,3:6,7]oxepino[4,5-c]pyrrole, its kinetics and metabolism, as well as the first safety and efficacy studies in human volunteers and in schizophrenic patients were reviewed by De Boer et al. (Drugs of the Future 1993, 18(12), 1117-1123). It has been established that asenapine is a very potent dopamine and serotonin antagonist with antipsychotic activity.

Funke et al (Arzneim.-Forsch./Drug Res. 40 (1999), 536-539) have described Physico-chemical properties of asenapine maleate. This known crystalline asenapine maleate (form H or monoclinic form) has a melting point of 141-145° C. and is typically comprised of crystalline particles over 100 µm in size as observed in micrographs.

A pharmaceutical composition comprising asenapine maleate for sublingual or buccal administration was described in WO 95/23600. For the development of a sublingual formulation, drug substance with a small particle size is desired. Therefore, to reduce the particle size of the crystals, a micronization step is applied. However, as described below, it is difficult to obtain drug substance with high polymorph purity by micronization of the monoclinic form of asenapine.

The particle size of the drug substance influences biopharmaceutical properties of the drug product. For example, the particle size of the drug substance affects drug product manufacturing and dissolution and hence its bioavailability. Since asenapine dissolves in the saliva the particle size is important. When drug substance particles are small, it takes only short periods of time to achieve high concentrations. From this perspective small particles are preferred. In addition, smaller particle size tends to improve the homogeneity of powder blends, which may result in improved uniformity of the contents of the drug product. For asenapine maleate, the particle size, in terms of d95, is preferably about 100 µm or less, more preferably about 50 µm or less, and most preferably about 30 µm or less. As used throughout the disclosure, the term d95 means that 95% of the particles (based on volume) are smaller than or equal to the indicated size.

Smaller particles of drug substance can be achieved by micronization. The outcome of the micronization process, however, appeared to be very unpredictable when crystals of the monoclinic form were subjected to such a process. Analyses of the crystals following micronization revealed the presence of a second polymorph (orthorhombic form L) in addition to the known monoclinic form in the starting material. Either the monoclinic form, or the orthorhombic form or a mixture of polymorphs was obtained after micronization starting with the monoclinic form. Even when the starting material was taken from the same batch of the monoclinic form of asenapine maleate, micronization resulted in product that was not reproducible (see examples 9 and 10).

In addition, drug substance with high polymorph purity could not be obtained by micronization of the monoclinic form of asenapine maleate.

It is generally desirable to prepare therapeutic agents of uniform and defined composition. If a mixture of polymorphic forms is used as a medicament great drawbacks are associated therewith as compared with a pure polymorphic form. The difference in crystal structure can lead to differences in physicochemical parameters such as stability, rate of dissolution, bioavailability, and the like. Hence, a mixture of polymorphic forms of a compound frequently has different physicochemical to parameters than the pure forms that comprise the mixture. This is all the more important since in practice it is difficult to make each batch of a mixture of polymorphs of a compound identical in respect of its composition. As a consequence of these differences, it is often undesirable to incorporate a mixture of polymorphs of a compound in medicaments which typically demand that only one of the polymorphs is used.

The present invention provides an orthorhombic form of asenapine maleate, which through the use of a special crystallization technique, can be prepared in a highly pure form. Furthermore, the non-comminuted orthorhombic form has a comparatively smaller particle size (based on d95) than the non-comminuted monoclinic form of asenapine maleate. Moreover, it has been found that micronization of the orthorhombic form of asenapione maleate reproducibly results in microcrystalline asenapine maleate of the orthorhombic form.

Thus one aspect of the invention provides an orthorhombic crystalline form of asenapine maleate, which contains 10% or less of another crystalline form, 5% or less of another crystalline form, or no detectable amount of another crystalline form, respectively.

Another aspect of the invention provides an orthorhombic crystalline form of asenapine maleate that is microcrystalline. Here the term "microcrystalline" means that the form comprises particles having a size distribution characterized by a d95 of 30 μm or less.

Yet another aspect of the invention provides a process for the preparation of the orthorhombic crystalline form of asenapine maleate. The process comprises crystallization of asenapine maleate by cooling from an ethanol/water mixture containing dissolved asenapine maleate. The mixture preferably is 9:1 v/v ethanol/water. Optionally, when crystals of the orthorhombic form are available, a solution of asenapine maleate in the ethanol/water mixture can be seeded with such crystals. The crystallized material may further be disaggregated or screened to remove clusters of micro crystals.

The crystalline asenapine maleate prepared according to the invention is a particular polymorphic form, which has a melting point in the range of 138-142° C.

The crystal of the orthorhombic form of the present invention can be characterized, and thus distinguished from the monoclinic form, by several analytical techniques known in the art such as Infrared Spectroscopy, Raman Spectroscopy, Solid State Nuclear Magnetic Resonance Spectroscopy, Differential Scanning Calorimetry, X-ray powder diffraction patterns (XPRD) and many others. Such techniques may be applied individually or in combination.

FIG. 1 depicts XRPD patterns for the monoclinc form (upper pattern) and the orthorhombic form (lower pattern) of asenapine maleate. Each of the patterns is characterized by intensity peaks at certain specific values of the diffraction angle 2 theta (θ). The monoclinic form has characteristic peaks at 2-theta=9.6°, 20.4°, 22.0°, 23.4°, 25.2°, 26.1°, 26.7°, 26.8, 29.1° and 30.0°, with the more characteristic peaks being at 9.6°, 20.4°, 22.0°, 23.4°, 25.2° and 26.8°. The most characteristic peaks are at 9.6° and 26.8°.

The orthorhombic form is characterized by peaks at 2-theta=10.5°, 15.7°, 18.3°, 19.0°, 20.3°, 20.8°, 22.2°, 23.2°, 25.6° and 27.5°, with the more characteristic peaks being at 10.5°, 15.7°, 18.3°, 19.0°, 22.2°, 23.2° and 27.5°. The most characteristic peaks are at 10.5° and 15.7°.

A 2-theta value as indicated typically means that specific value ±0.2.

The orthorhombic form can also be characterized by its crystallographic data. Crystallographic data of the orthorhombic and monoclinic form obtained by single-crystal X-ray diffraction have been compared to each other. It was established that the crystal structure belonging to the monoclinic form consists of the space group $P2_1/n$ and 4 molecules in the unit cell, whereas the crystal structure belonging to the orthorhombic form consists of the space group $Pca2_1$ and 8 molecules in the unit cell. The data are shown in Tables 1a and 1b. An axis length in Table 1a typically means that specific value ±0.2 Å. A cell angle in Table 1a typically means that value ±0.2°. An atomic position (x, y, z) in Table 1b typically means those values ±0.002.

TABLE 1A

Crystallographic data concerning the unit cells of asenapine maleate monoclinic form and orthorhombic form

| | Monoclinic form | Orthorhombic form |
|---|---|---|
| Space group | $P2_1/n$ | $Pca2_1$ |
| Z | 4 | 8 |
| a (Å) | 17.8 | 11.0 |
| b (Å) | 11.0 | 20.2 |

TABLE 1A-continued

Crystallographic data concerning the unit cells of asenapine maleate monoclinic form and orthorhombic form

| | Monoclinic form | Orthorhombic form |
|---|---|---|
| c (Å) | 10.3 | 17.3 |
| α (°) | 90 | 90 |
| β (°) | 101.0 | 90 |
| γ (°) | 90 | 90 |
| V (Å³) | 1976 | 3824 |
| $D_c$ (g cm$^{-3}$) | 1.35 | 1.40 |

The crystallographic data from Tables 1A and 1B can be used to calculate X-ray powder diffraction patterns (XRPD patterns) of the monoclinic form and of the orthorhombic form of asenapine maleate. These calculated XRPD patterns of the monoclinic form and orthorhombic form of asenapine maleate can be used to compare with experimental patterns. Furthermore, the data from Table 1a can be used for a Pawley fit to compare experimental XRPD patterns to the crystallographic data of the monoclinic and orthorhombic form of asenapine maleate. Even more, the data from Table 1b can be used for a Rietveld Refinement to compare experimental XRPD patterns to the crystallographic data of the monoclinic and orthorhombic form of asenapine maleate.

The crystal of the orthorhombic form of the present invention can also be characterized, and thus distinguished from the monoclinic form, by their Raman spectra.

FIG. 2 depicts Raman spectra for monoclinc form (upper spectrum) and orthorhombic form (lower spectrum) of asenapine maleate.

TABLE 1B

Crystallographic data concerning the fractional atomic positions of asenapine maleate monoclinic form and orthorhombic form

| Monoclinic form | | | | Orthorhombic form | | | |
|---|---|---|---|---|---|---|---|
| atom | x | y | z | atom | x | y | z |
| N | 0.7358 | 0.3853 | 0.1998 | N | 0.0882 | 0.1628 | 0.2804 |
| Cl | 0.4562 | 0.1357 | 0.4683 | Cl | 0.2828 | −0.0176 | −0.0076 |
| O | 0.5082 | 0.6250 | 0.2880 | O | −0.1458 | −0.0394 | 0.1668 |
| O | 0.2213 | 0.2168 | 0.4130 | O | 0.6740 | 0.2238 | 0.0820 |
| O | 0.2148 | 0.3418 | 0.5767 | O | 0.8039 | 0.2030 | 0.1658 |
| O | 0.1918 | 0.3674 | 0.0222 | O | 0.6810 | 0.2732 | −0.0309 |
| O | 0.2124 | 0.2255 | 0.1745 | O | 0.8217 | 0.3188 | −0.0987 |
| C | 0.6925 | 0.3634 | 0.3095 | C | −0.0373 | −0.0366 | 0.1285 |
| C | 0.6283 | 0.4583 | 0.2908 | C | −0.0233 | −0.0883 | 0.0727 |
| C | 0.5546 | 0.4192 | 0.3302 | C | 0.08133 | −0.0807 | 0.0326 |
| C | 0.4951 | 0.5053 | 0.3174 | C | 0.1576 | −0.0253 | 0.0457 |
| C | 0.5233 | 0.6628 | 0.1686 | C | 0.1478 | 0.0243 | 0.0979 |
| C | 0.5739 | 0.6068 | 0.1009 | C | 0.0479 | 0.0182 | 0.1397 |
| C | 0.6168 | 0.4892 | 0.1436 | C | 0.0327 | 0.0700 | 0.1998 |
| C | 0.6986 | 0.4912 | 0.1216 | C | 0.1111 | 0.1377 | 0.2085 |
| C | 0.8191 | 0.4003 | 0.2426 | C | 0.0042 | 0.2304 | 0.2844 |
| C | 0.5417 | 0.3050 | 0.3766 | C | 0.0412 | 0.0918 | 0.3158 |
| C | 0.4704 | 0.2787 | 0.4075 | C | 0.0409 | 0.0281 | 0.2624 |
| C | 0.4126 | 0.3625 | 0.3904 | C | −0.0561 | −0.0353 | 0.2780 |
| C | 0.4253 | 0.4761 | 0.3477 | C | −0.0564 | −0.0657 | 0.3412 |
| C | 0.4869 | 0.7719 | 0.1217 | C | −0.1415 | −0.1239 | 0.3604 |
| C | 0.5008 | 0.8240 | 0.0104 | C | −0.2254 | −0.1491 | 0.3134 |
| C | 0.5508 | 0.7718 | −0.0586 | C | −0.2204 | −0.1209 | 0.2504 |
| C | 0.5858 | 0.6647 | −0.0133 | C | −0.1360 | −0.0650 | 0.2325 |
| C | 0.2015 | 0.4272 | 0.3663 | C | 0.7791 | 0.2274 | 0.1077 |
| C | 0.2133 | 0.3209 | 0.4577 | C | 0.8836 | 0.2608 | 0.0697 |
| C | 0.1969 | 0.4327 | 0.2377 | C | 0.8897 | 0.2887 | 0.0086 |
| C | 0.2008 | 0.3373 | 0.1384 | C | 0.7927 | 0.2950 | −0.0432 |

Each of the spectra is characterized by intensity peaks at certain specific values of wave number (cm$^{-1}$). The monoclinic form has characteristic peaks at 3070 cm$^{-1}$, 3020 cm$^{-1}$, 2900 cm$^{-1}$, 2871 cm$^{-1}$, 2829 cm$^{-1}$, 1253 cm$^{-1}$, 1238 cm$^{-1}$, 849 cm$^{-1}$, 743 cm$^{-1}$ and 711 cm$^{-1}$, with the more characteristic peaks being at 3070 cm$^{-1}$, 3020 cm$^{-1}$, 2871 cm$^{-1}$, 849 cm$^{-1}$ and 711 cm$^{-1}$. The most characteristic peaks are at 2871 cm$^{-1}$ and 849 cm$^{-1}$.

The orthorhombic form is characterized by peaks at 3072 cm$^{-1}$, 3051 cm$^{-1}$, 3029 cm$^{-1}$, 3011 cm$^{-1}$, 2909 cm$^{-1}$, 2888 cm$^{-1}$, 1245 cm$^{-1}$, 824 cm$^{-1}$, 747 cm$^{-1}$, 717 cm$^{-1}$ and 194 cm$^{-1}$, with the more characteristic peaks being at 3051 cm$^{-1}$, 3029 cm$^{-1}$, 3011 cm$^{-1}$, 2888 cm$^{-1}$, 824 cm$^{-1}$ and 717 cm$^{-1}$. The most characteristic peaks are at 2888 cm$^{-1}$ and 824 cm$^{-1}$.

A wave number value as indicated above typically means that specific value ±2 cm$^{-1}$.

The newly found advantageous property provides as a further aspect of the invention the use of asenapine maleate in the orthorhombic form for the preparation of fine crystal suspensions.

A further aspect of the invention provides pharmaceutical preparations comprising the orthorhombic crystalline form of asenapine maleate in association with one or more pharmaceutically acceptable additives or excipients. In addition to the orthorhombic crystalline form, amorphous asenapine maleate may be present.

Such pharmaceutical preparations generally take the form of a dosage unit such as a tablet, a capsule or a suppository, but other solid or dry pharmaceutical preparations are included. A preferred pharmaceutical preparation is in the form of a tablet. A tablet may contain certain excipients in addition to the active principle asenapine maleate in the crystalline orthorhombic form such as diluents, binders, glidants and lubricants, which serve to impart satisfactory processing and compression characteristics to the tablet, as well as disintegrants and flavoring agents, which gives additional desirable physical characteristics to the finished tablet.

Methods for making such dosage units are well known, for example in accordance with standard techniques such as those described in the standard reference, Gennaro et al., Remington's Pharmaceutical Sciences, (18th ed., Mack Publishing Company, 1990, especially Part 8: Pharmaceutical Preparations and Their Manufacture).

A dosage unit of asenapine maleate, suitable for the treatment of mental disorders such as psychosis, bipolar disorders and schizophrenia may contain from about 0.005 to 500 mg of the active ingredient. A preferred dosage unit may contain 1-50 mg of asenapine maleate in the crystalline orthorhombic form.

The invention is illustrated by the following, non-limiting examples.

EXAMPLES

General Methods

Figure 1:
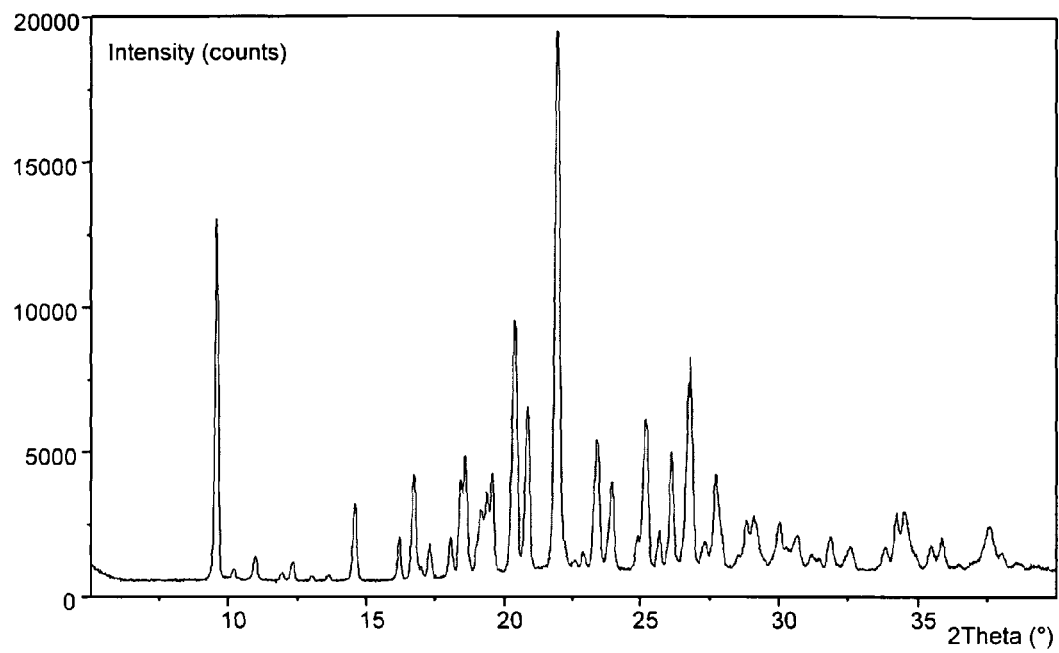
FIG. 1 shows XRPD patterns of the monoclinic form (upper) and the orthorhombic form (lower) of trans-5-chloro-2-methyl-2,3,3a,12b-tetrahydro-1H-dibenz[2,3:6,7]-oxepino[4,5-c]pyrrole (Z)-2-butenedioate measured in reflection.
Figure 1:
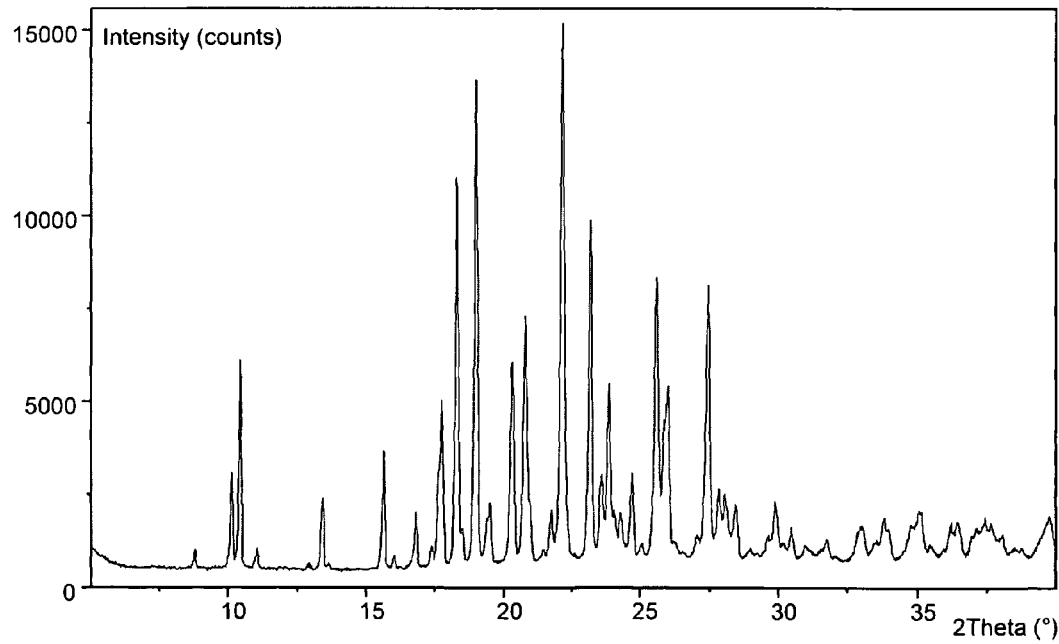
Figure 2:
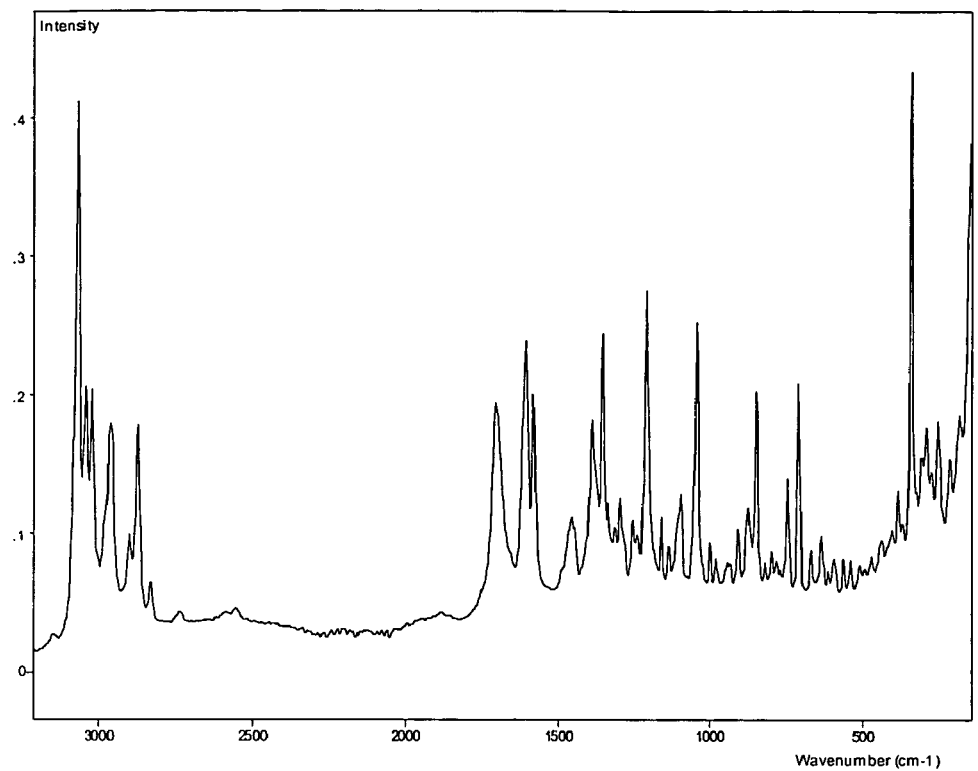
FIG. 2 shows Raman spectra of the monoclinic form (upper) and the orthorhombic form (lower) of trans-5-chloro-2-methyl-2,3,3a,12b-tetrahydro-1H-dibenz[2,3:6,7]-oxepino[4,5-c]pyrrole (Z)-2-butenedioate.
Figure 2:
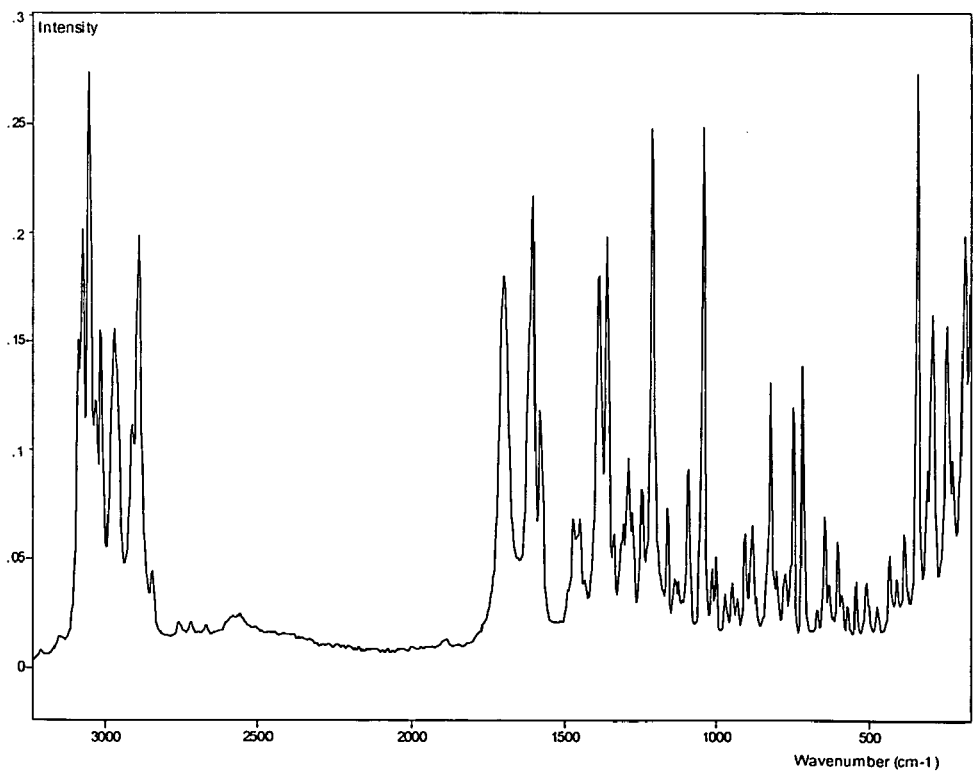

X-ray powder diffraction (XRPD) spectra were obtained on a XPert pro Panalytical Reflection diffractometer in a Bragg-Brantano setup, Cu—Kα radiation, settings 45 kV and 40 mA together with a X'celerator detector. The slits used: anti-scatter slit 1°, divergence slit ½°, soller slits 0.02 rad. Measuring conditions: scan range 5-40° 2-theta, step size 0.0167° 2-theta. The samples were measured on a rotating sample disk of Si with a speed of 15 rpm. The XRPD spectra of crystalline pure monoclinic form and pure orthorhombic form are depicted in FIG. 1.

Single crystal structure measurements. The measured crystals were fixed with inert perfluoro-oil to the tip of a Lindemann-glass capillary and transferred into the cold nitrogen stream on a Nonius KappaCCD on rotating anode. The structures were solved by direct methods (SHELX86) and refinements on $F^2$ were carried out by full-matrix least-squares techniques (SHELXL-97-2); no observance criteria were applied during refinement. Neutral atom scattering factors and anomalous dispersion corrections were taken from the International Tables for Crystallography. Geometrical calculations and illustrations were performed with PLATON. All calculations were performed on a Transtec 3.0 GHz Xeon PC under Debian Linux.

The FT-Raman spectra were recorded using a Bruker RFS 100/S FT-Raman spectrometer equipped with a 1064 nm Adlas DPY 421 Nd:YAG laser with a maximum power of 1550 mW and a liquid nitrogen cooled Ge detector. For each sample, 128 scans were collected using a focussed beam (laserspot 100 μm), a laserpower of 150 mW and a resolution of 2 cm$^{-1}$.

LDS method. A dispersion liquid has been made consisting of (0.7 mg/ml) lecithin (used as a surfactant) in iso-octane saturated with asenapine maleate. The solution is stirred overnight. Subsequently the solution is filtered over a 0.22 μm filter. The samples were prepared by weighing approximately 30 mg asenapine maleate in a centrifugal tube and adding 2 ml of the dispersion liquid. Ultrasonic treatment of the samples was performed for 2 minutes in an ultrasonic bath (Transsonic 310). Subsequently, the particle size distribution of the sample was analyzed using laser diffraction (Malvern Mastersizer S, UK). The particle size distribution has been calculated using the Fraunhofer algorithm.

DSC Method. Differential Scanning Calorimetry (DSC) has been used for the determination of the melting point (onset temperature in ° C.) of asenapine maleate. The DSC equipment contained a measuring cell based on heat flux principle with a ceramic sensor and a furnace supply which can be used in the temperature range 0 to 300° C. The heating rate was at least in the range of 1-20° C./min. Purge gas was nitrogen ($N_2$) with a controlled flow of 50 mL/min. Asenapine maleate drug substance (2-5 mg) was accurately weighed in an aluminum sample pan. The applied heating rate was 5° C./min and the temperature program was linear from 0-250° C.

Example 1

Synthesis of asenapine maleate from asenapine and maleic acid

The free base compound (I), trans-5-chloro-2,3,3a,12b-tetrahydro-2-methyl-1H-dibenz [2,3:6,7]oxepino[4,5-c]pyrrole (30 kg), was dissolved in 60 L of ethanol and evaporated in vacuum at 65° C. Ethanol (90 L) was added to the residue and 1.8 kg of charcoal was added to the solution at 60° C. Stirring was continued for 30 minutes at 60° C. and the solution was filtered dust free on filter aid. The filter aid was washed with 30 L of ethanol of 60° C. At 60° C., a solution of 13.5 kg of maleic acid in 90 L of ethanol was added to the combined filtrates and stirring was continued for 30 minutes. The reaction mixture was cooled to 20° C. and stirred for 2 hours. The reaction mixture was then cooled to −10° C. (±2° C.), stirred for 2 hours and the crystals were filtered. The crystals were washed with 5 L of ethanol (−10° C.) and collected. The wet crystals are directly used in the recrystallization which is described in examples 2-8.

Example 2

Crystallization of Batch C1 (Monoclinic Polymorph)

Asenapine maleate (10 kg) prepared according to the procedure described in example to 1 was dissolved in 24 L of ethanol at boiling temperature. After cooling at 20° C. the solution was stirred for 1 hour and cooled to −10° C. (±2° C.). Stirring was continued for 2 hours, the crystals were collected and washed twice with 3.5 L of cold (−10° C.) ethanol. The impurity profile of the product was determined by GLC analysis. The crystals were dried in vacuum at 60° C.
Yield: 10 kg=100% (m/m) of trans-5-chloro-2,3,3a,12b-tetrahydro-2-methyl-1H-dibenz [2,3:6,7]oxepino[4,5-c]pyrrole (Z)-2-butenedioate (1:1) (asenapine maleate 2).
DSC: 140.6° C.
XRPD: complies to reference of monoclinic polymorph
Polymorphic purity: ~90% monoclinic form and 10% orthorhombic form
Particle size by LDS: d95<19 μm Example 3

Crystallization of Orthorhombic Polymorph

Asenapine maleate (260 g) as prepared according to example 1 was dissolved in a mixture of ethanol (480 ml) and water (50 ml) by heating to 57° C. Then the solution was slowly allowed to cool and crystallization started. After stirring for 72 hours the reaction mixture was cooled to −10° C. and stirred for another hours. Then the crystals were collected by filtration. This provided asenapine maleate orthorhombic form (224 g, 86%).
XRPD: >95% orthorhombic form Example 4

Crystallization of Batch C2 (Monoclinic Polymorph)

Another batch was prepared according to example 2.
Yield: 10 kg=100% (m/m) asenapine maleate.
DSC: 141.0° C.
XRPD: complies to reference of monoclinic polymorph
Polymorphic purity: >95% monoclinic form
Particle size by LDS: d95<221 μm Example 5

Crystallization of Batch C3 (Orthorhombic Polymorph)

Asenapine maleate (~30 kg) prepared according to the procedure described in example 1, was dissolved in 57 L of ethanol and 6.5 L of demineralized water at 55° C. The solution was filtered dust free and the filtrate is cooled slowly to 20±5° C. The filtrate was seeded with 30 g of Org 5222 (polymorphic orthorhombic form) and cooled to for 48±6 hours at 20±5° C. The crystals were collected and dried in vacuum at 60° C.
Yield: 20.06 kg=69% (m/m) of asenapine maleate.
DSC: 139.1° C.
XRPD: complies to reference of the orthorhombic polymorph >95% pure Example 6

Crystallization of Batch C4 (Orthorhombic Polymorph)

The procedure was as described under example 5 with 28.9 kg of asenapine free base.
Yield: 20.88 kg=72% (m/m) of asenapine maleate (1, orthorhombic form).
DSC: 139.2° C.
XRPD: complies to reference of orthorhombic polymorph >95% pure Example 7

Crystallization of Batch C5 (Orthorhombic Polymorph)

The procedure was as described under example 4 with 26.9 kg of asenapine free base.
Yield: 22.85 kg=85% (m/m) of asenapine maleate (1, orthorhombic form).
DSC: 139.9° C.
XRPD: complies to reference of orthorhombic polymorph >95% pure
LDS: average particle size ~30 μm
Microscopic picture: particle up to 100 μm Example 8

Crystallization of Batch C6 (Orthorhombic Polymorph)

The procedure was as described under example 5 with 28.9 kg of asenapine free base.
Yield: 24.2 kg=84% (m/m) of asenapine maleate.
DSC: 139.2° C.
XRPD: complies to reference of orthorhombic polymorph >95% pure Example 9-15

Micronization of Batches C1-C6 to Give M1-M6

The pure products of batches C1 through C6 as described in examples 2, and 4-8 were micronized in a Chrispro MC200 stainless steel Jet Mill, using nitrogen as the carrier gas and a micronization pressure of 7 bar.
The results are shown in Table 2.
It was demonstrated that micronization of crystals of asenapine maleate of the orthorhombic polymorph consistently takes place with retention of the polymorphic form. This is evidenced by the results of the micronization of batches C3-C5, which furnished the micronized batches M4, M5, M6, and M7 (examples 12-15). The micronized batches M4-M7 all were characterized as the orthorhombic polymorph with a small particle i.e.: d95<30 μm, as is shown in Table 2. In addition, the polymorphic purity of the product is very high (>95% orthorhombic form) as substance of the monoclinic polymorph could not be detected by XRPD.

Example 16

Pharmaceutical Composition

Principle

Asenapine maleate of the orthorhombic form was mixed into a gelatin/mannitol matrix and dosed by weight into preformed pockets. The matrix was frozen within the pockets by passage through a freeze tunnel. The frozen tablets were then dried by sublimating the ice in a freeze dryer.

Procedure for the Manufacture 2000 g Gelatin and 1500 g mannitol were dispersed in 45.01 kg of purified water, while stirring and heating in a vacuum mixer. After dissolution the matrix was filtered, 1406 g trans-5-chloro-2,3,3a,12b-tetrahydro-2-methyl-1H-dibenz[2,3:6,7]oxepino[4,5-c]pyrrole (Z)-2-butenedioate orthorhombic form was added and mixed. The mixture was dispensed using dosing pumps into preformed blister pockets (250 mg in each pocket). The filled pockets were frozen by passing through a liquid nitrogen freeze tunnel. The frozen tablets were dried in a freeze dryer using a pre-programmed drying cycle. Each pocket contained a pharmaceutical unit dosage comprising 7.03 mg of trans-5-chloro-2,3,3a,12b-tetrahydro-2-methyl-1H-dibenz[2,3:6,7]oxepino[4,5-c]pyrrole (Z)-2-butenedioate, 10.0 mg gelatin and 7.5 mg mannitol.

Example 17

Recrystallization to Obtain Orthorhombic Form

Crude asenapine maleate monoclinic form (20 kg) was dissolved in acetone (87.6 kg) and heated to 55° C. The solution was passed through a filter to remove undissolved materials. Heptane (25.5 kg) was added and the temperature was returned to 55° C. Seed crystals of asenapine maleate orthorhombic form (approximately 100 g) were added and stirred for 1 hour. Thereafter heptane (62.8 kg) was added at a constant rate over 2 hours. After stirring the mixture at 57° C. for 2 hours, the temperature was brought to 10° C. over 6 hours. Asenapine maleate was isolated by filtration and washed with a 1:1 mixture of acetone and heptane (30 kg) cooled to 10° C. The material was thereafter dried. The yield was 90-96%. XPRD analysis showed that >95% orthorhombic form was obtained.

The invention claimed is:

1. Orthorhombic trans-5-chloro-2,3,3a,12b-tetrahydro-2-methyl-1H-dibenz[2,3:6,7]oxepino[4,5-c]pyrrole (Z)-2-butenedioate isolated in a form which contains at least about 90 wt. % of the orthorhombic crystalline form.

2. The compound according to claim 1 which is characterized by an X-ray powder diffraction pattern obtained with CuKα radiation with peaks at values of 2-theta (2θ) of 10.5°, 15.7°, 18.3°, 19.0°, 22.2°, 23.2° and 27.5°.

3. The compound according to claim 1 which is characterized by an X-ray powder diffraction pattern obtained with CuKα radiation with peaks at values of 2-theta (2θ) of 10.5°, 15.7°, 18.3°, 19.0°, 20.3°, 20.8°, 22.2°, 23.2°, 25.6° and 27.5°.

4. The compound according to claim 1 which is characterized by a Raman spectroscopic pattern with peaks at values of 3051 cm$^{-1}$, 3029 cm$^{-1}$, 3011 cm$^{-1}$, 2888 cm$^{-1}$, 824 cm$^{-1}$ and 717 cm$^{-1}$.

5. The compound according to claim 1 which is characterized by a Raman spectroscopic pattern with peaks at values of 3072 cm$^{-1}$, 3051 cm$^{-1}$, 3029 cm$^{-1}$, 3011 cm$^{-1}$, 2909 cm$^{-1}$, 2888 cm$^{-1}$, 1245 cm$^{-1}$, 824 cm$^{-1}$, 747 cm$^{-1}$, 717 cm$^{-1}$ and 194 cm$^{-1}$.

6. A method of preparation of the compound according to claim 1 characterized in that trans-5-chloro-2,3,3a,12b-tetrahydro-2-methyl-1H-dibenz [2,3:6,7]oxepino[4,5-c]pyrrole (Z)-2-butenedioate is crystallized from an ethanol/water mixture.

7. A pharmaceutical composition comprising a pharmaceutically acceptable excipient and trans-5-chloro-2,3,3a,12b-tetrahydro-2-methyl-1H-dibenz [2,3:6,7]oxepino[4,5-c]pyrrole (Z)-2-butenedioate in the orthorhombic crystal form, wherein said composition is prepared by using the trans-5-chloro-2,3,3a,12b-tetrahydro-2-methyl-1H-dibenz[2,3:6,7]oxepino[4,5-c]pyrrole (Z)-2-butenedioate of claim 1.

8. A method of treating a mental disorder selected from schizophrenia and bipolar disorder in a mammal, comprising administering a therapeutically effective amount of a composition of claim 7.

9. The method according to claim 8, wherein the mammal is a human.

10. Then method according to claim 8, wherein the mental disorder is schizophrenia.

11. The method according to claim 8, wherein the mental disorder is bipolar disorder.

\* \* \* \* \*

TABLE 2

| | Micronization of asenapine maleate | | | | | | |
|---|---|---|---|---|---|---|---|
| Example | Crystallization sample | D95 (μm) | DSC polymorph | Micronization sample | D95 (μm) | DSC | polymorph |
| 9 | C1 | 199 | 140.6 monoclinic | M1 | <12 | | >95% orthorhombic |
| 10 | C2 | 221 | 141 monoclinic | M2 | <14 | 141 | >95% monoclinic |
| 11 | C2 | | 141 monoclinic | M3 | <16 | 138 | 80% orthorhombic, 20% monoclinic |
| 12 | C3 | | 139.1 orthorhombic | M4 | <9 | 138.2 | >95% orthorhombic |
| 13 | C4 | | 139.2 orthorhombic | M5 | <6 | 139.2 | >95% orthorhombic |
| 14 | C5 | 30-100 | 139.9 orthorhombic | M6 | <10 | 139.9 | >95% orthorhombic |
| 15 | C6 | | 139.2 orthorhombic | M7 | <12 | 139.2 | >95% orthorhombic |